(12) United States Patent
Norfray

(10) Patent No.: US 8,197,795 B2
(45) Date of Patent: *Jun. 12, 2012

(54) METHOD FOR MONITORING EARLY TREATMENT RESPONSE

(75) Inventor: Joseph F. Norfray, Glenview, IL (US)

(73) Assignee: Receptomon, LLC, Glenview, IL (US)

( * ) Notice: Subject to any disclaimer, the term of this patent is extended or adjusted under 35 U.S.C. 154(b) by 1131 days.

This patent is subject to a terminal disclaimer.

(21) Appl. No.: 11/576,198

(22) PCT Filed: Jul. 29, 2005

(86) PCT No.: PCT/US2005/027060
§ 371 (c)(1),
(2), (4) Date: May 25, 2007

(87) PCT Pub. No.: WO2006/036288
PCT Pub. Date: Apr. 6, 2006

(65) Prior Publication Data
US 2007/0218006 A1    Sep. 20, 2007

Related U.S. Application Data

(63) Continuation-in-part of application No. 10/946,741, filed on Sep. 22, 2004, now Pat. No. 7,289,840.

(51) Int. Cl.
*A61K 49/00* (2006.01)
(52) U.S. Cl. ...................................................... 424/9.2
(58) Field of Classification Search ................ 424/1.11, 424/1.65, 1.73, 1.81, 1.85, 1.89, 9.1, 9.2, 424/9.3, 9.31, 9.32, 9.322, 9.323, 9.34, 9.341, 424/9.35, 9.351, 9.36, 9.361, 9.362, 9.363, 424/9.364, 9.365, 9.37; 600/407, 410
See application file for complete search history.

(56) References Cited

U.S. PATENT DOCUMENTS

| | | |
|---|---|---|
| 4,354,499 A | 10/1982 | Damadian |
| 4,411,270 A | 10/1983 | Damadian |
| RE32,619 E | 3/1988 | Damadian |
| RE32,689 E | 6/1988 | Damadian |
| 4,843,321 A | 6/1989 | Sotak |
| 4,962,357 A | 10/1990 | Sotak |
| 5,111,819 A | 5/1992 | Hurd |
| 5,200,345 A | 4/1993 | Young |
| 5,220,302 A | 6/1993 | Nunnally et al. |
| 5,498,421 A | 3/1996 | Grinstaff et al. |
| 5,578,921 A | 11/1996 | Morrell |
| 5,585,118 A | 12/1996 | Stoll |
| 5,617,861 A | 4/1997 | Ross et al. |
| 5,887,588 A | 3/1999 | Usenius et al. |
| 5,903,149 A | 5/1999 | Gonen et al. |
| 6,046,589 A | 4/2000 | Lamerichs et al. |
| 6,181,134 B1 | 1/2001 | Wald |
| 6,280,383 B1 | 8/2001 | Damadian |
| 6,347,239 B1 | 2/2002 | Arnold et al. |
| 6,400,150 B1 | 6/2002 | Liu et al. |
| 6,617,169 B2 | 9/2003 | Ke et al. |
| 6,630,125 B2 | 10/2003 | DeGrado et al. |
| 6,639,405 B2 | 10/2003 | Liu et al. |
| 6,681,132 B1 | 1/2004 | Katz et al. |
| 6,708,053 B1 | 3/2004 | Brooks et al. |
| 6,756,063 B2 | 6/2004 | Kiss |
| 6,819,952 B2 | 11/2004 | Pfefferbaum et al. |
| 6,838,877 B2 | 1/2005 | Heid et al. |
| 7,289,840 B2 * | 10/2007 | Norfray .................... 600/410 |
| 7,572,448 B2 | 8/2009 | Thorpe et al. |
| 7,622,102 B2 * | 11/2009 | Norfray .................... 424/9.3 |
| 7,771,706 B2 * | 8/2010 | Norfray .................... 424/9.2 |
| 2001/0003423 A1 | 6/2001 | Wald |
| 2002/0142367 A1 | 10/2002 | Ke et al. |
| 2002/0173713 A1 | 11/2002 | Pfefferbaum et al. |
| 2003/0028093 A1 | 2/2003 | Ke et al. |
| 2003/0199751 A1 | 10/2003 | Gonzalez et al. |
| 2003/0208120 A1 | 11/2003 | Thomas et al. |
| 2003/0214292 A1 | 11/2003 | Heid et al. |
| 2004/0092809 A1 | 5/2004 | DeCharms |
| 2005/0031620 A1 | 2/2005 | Thorpe et al. |

(Continued)

FOREIGN PATENT DOCUMENTS
WO    WO 2006/036288    4/2006
(Continued)

OTHER PUBLICATIONS

Neeman et al (Proc. Natl. Acad. Sci. USA, 1989, vol. 86, pp. 5585-5589).*
Chung et al (J. Nat. Cancer Inst., 2003, vol. 95, No. 21, pp. 1624-1633).*
Farhadi, et al., "Combined Inhibition of Vascular Endothelial Growth Factor and Platelet-Derived Growth Factor Signaling: Effects on the Angiogenesis, Microcirculation, and Growth of Orthotopic Malignant Gliomas", *Journal of Neurosurgery*, 102:363-370 (Feb. 2005).
Laird et al., *Cancer Research*, 2000, vol. 60, pp. 4152-4160.
Mukherji et al., *AJNR Am. J. Neuroradio.*, 1996, vol. 17, pp. 1485-1490.
Balkwill et al., *The Lancet*, 357, 539-545 (2001).
Becker, et al., *The World of the Cell, Third Edition*, The Benjamin/Cummings Publishing Company, Ch. 9, 229-270, (1996).

(Continued)

*Primary Examiner* — D L Jones
(74) *Attorney, Agent, or Firm* — Leydig, Voit & Mayer, Ltd.

(57) ABSTRACT

Disclosed is a method for monitoring early treatment response of a cancer treatment comprising measuring by magnetic resonance spectroscopy (MRS), for example, proton MRS, the amount of Choline present in the cancerous tissue before and after treatment; the treatment comprises administration of a cell surface receptor inhibitor, for example, an EGFR inhibitor, whereby a decrease in the amount of Choline after treatment is indicative of a positive response. The decrease in the amount of Choline represents the decrease in the internal cell membrane as a result of down regulation of the organelles and their secretory granules and their transport vesicles. Disclosed also is a method for determining effectiveness of a cell surface receptor inhibitor in the treatment of cancer. Further, the present invention provides for a method for monitoring protein translation in an animal having a cancerous tissue by MRS.

25 Claims, No Drawings

U.S. PATENT DOCUMENTS

| | | |
|---|---|---|
| 2005/0107683 A1 | 5/2005 | Mountford et al. |
| 2006/0035945 A1 | 2/2006 | Attardo et al. |
| 2006/0064003 A1 | 3/2006 | Norfray |
| 2006/0177377 A1 | 8/2006 | Norfray |
| 2006/0177378 A1 | 8/2006 | Norfray |
| 2006/0222591 A1 | 10/2006 | Norfray |
| 2007/0128114 A1 | 6/2007 | Norfray |

FOREIGN PATENT DOCUMENTS

| | | |
|---|---|---|
| WO | WO 2006/086159 | 8/2006 |
| WO | WO 2006/107950 | 10/2006 |

OTHER PUBLICATIONS

Bianco et al., *British Journal of Cancer*, 89, (Suppl. 2) (2003) S25-S35 Abstract.
Blackledge et al., *British Journal of Cancer*, 90, 566-572 (2004).
Bluml et al., *Magn. Reson. Med.*, 42, 643-654 (1999).
Boyer, *British Journal of Cancer*, 89, (Suppl. 2) (2003) S25-S35 Abstract.
Bunz et al., *The Journal of Clinical Investigation*, 104(3), 263-269 (Aug. 1999).
Cappuzzo et al. *I British Journal of Cancer*, 89, (Suppl. 2) (2003) S25-S35 Abstract.
Cappuzzo et al. *II British Journal of Cancer*, 89, (Suppl. 2) (2003) S25-S35 Abstract.
Chioni et al., *British Journal of Cancer*, 89, (Suppl. 2) (2003) S25-S35 Abstract.
Colman, *Semin. Thromb. Hemost.*, 30(1), 45-61 (2004).
Cortes-Funes et al., *British Journal of Cancer*, 89, (Suppl. 2) (2003) S25-S35 Abstract.
Daly et al., *The Journal of Biological Chemistry*, 262(31) 14875-14878 (Nov. 5, 1987).
Danielsen et al., *Magnetic Resonance Spectroscopy Diagnosis of Neurological Diseases*, Marcel Dekker, Inc. Ch.3: The clinical significance of metabolites, 23-43 (1999).
de Braud et al., *British Journal of Cancer*, 89, (Suppl. 2) (2003) S25-S35 Abstract.
DeClerck et al., *Am. J. Pathol.*, 164(4), 1131-1139 (Apr. 2004).
de la Cruz et al., *I British Journal of Cancer*, 89, (Suppl. 2) (2003) S25-S35 Abstract.
de la Cruz et al., *II British Journal of Cancer*, 89, (Suppl. 2) (2003) S25-S35 Abstract.
de Leeuw et al., *British Journal of Cancer*, 89, (Suppl. 2) (2003) S25-S35 Abstract.
Diaz-Canton, *British Journal of Cancer*, 89, (Suppl. 2) (2003) S25-S35 Abstract.
Dieriks et al., *British Journal of Cancer*, 89, (Suppl. 2) (2003) S25-S35 Abstract.
Dzik-Jurasz, *The British Journal of Radiology*, Special Issue (2003) S81-S82.
Eliason et al., *Current Drug Targets*, 5, 383-388 (2004).
Enclyclopaedia Britannica, *The New Encyclopaedia Britannica*, 15th Edition, 565-593 (1994).
Engelse et al., *Semin. Thromb. Hemost.*, 30(1), 71-82 (2004).
Erlich, *I Drugs*, 6(4), 331-333 (2003).
Evelhoch, *Cancer Research*, 47, 3396-3401 (Jul. 1, 1987).
Farhadi et al. *Journal of Neurosurgery*, 102(2), 363-370 (Feb. 2005) Abstract.
Fernandez et al., *Semin. Thromb. Hemost.*, 30(1), 31-44 (2004).
Fisher et al., *Neuroimg. Clin. N. Am.* 12, 477-499 (2002).
Fujimoto et al., "A new immunological parameter predicting the efficacy of cancer therapy", *Editorial, Annals of Cancer Research and Therapy*, 7(2) (Title Only).
Fujimoto et al., *The 11th International Congress of Immunology* (2001) (Abstract).
Fukuoka et al, *Journal of Clinical Oncology*, 21(12) 2237-2246 (Jun. 15, 2003).
Fulham et al., *Radiology*, 185, 675-686 (1992).
Fuller et al., *Molecular Basis of Medical Cell Biology* (a Lange medical book), Ch. 4 67-92 (1998).
Galbraith, *The British Journal of Radiology*, 76, S83-S86 (2003).
Gelibter et al., *British Journal of Cancer*, 89, (Suppl. 2) (2003) S25-S35 Abstract.
Gervais et al., *British Journal of Cancer*, 89, (Suppl. 2) (2003) S25-S35 Abstract.
Griffiths et al. *The Lancet*, 1435-1436, (Jun. 25, 1983).
Harrigan, *Neurosurgery*, 53(3), 639-660 (2003).
International Searching Authority, "International search report" and "Written opinion of the International Searching Authority," for International Application No. PCT/US05/27060, mailed Jan. 24, 2007.
International Searching Authority, "International search report" and "Written opinion of the International Searching Authority," for International Application No. PCT/US06/02675, mailed Sep. 21, 2006.
International Searching Authority, "International search report" and "Written opinion of the International Searching Authority," for International Application No. PCT/US06/012469, mailed Mar. 13, 2007.
Jin et al., *Br. J. Cancer*, 90, 561-565 (2004).
Kauppinen, *NMR Biomedicine, NMR Biomed.*, 15, 6-17 (2002).
Katz et al., *British Journal of Cancer*, 89 (Suppl. 2) (2003) S25-S35 Abstract.
Kowalski et al., *British Journal of Cancer*, 89, (Suppl. 2) (2003) S25-S35 Abstract.
Kreis et al., *J. Magnetic Resonance Series B*, 102, 9-19 (1993).
Leach, et al. *British Journal of Cancer*, 92(9) 1599-1610 (2005).
Lynch et al., *New England Journal of Medicine*, 350(21), 2129-2139 (May 20, 2004).
Maione et al., *British Journal of Cancer*, 89, (Suppl. 2) (2003) S25-S35 Abstract.
Mancuso et al., *British Journal of Cancer*, 89, (Suppl. 2) (2003) S25-S35 Abstract.
Martin-Algarra et al., *British Journal of Cancer*, 89, (Suppl. 2) (2003) S25-S35 Abstract.
Martinez, *British Journal of Cancer*, 89, (Suppl. 2) (2003) S25-S35 Abstract.
Matsumoto et al., *Jpn. J. Clin. Oncol*, 34(3), 124-130 (2004).
Nakagami et al. *Jpn. Journal of Cancer Research*, 90 419-424 (Apr. 1999).
Negendank, *NMR in Biomedicine*, 5, 303-324 (1992).
Negendank, *Radiology*, 185, 875-883 (1992).
Nie et al., *Semin, Thromb. Hemost.* 30(1), 119-125 (2004).
Norfray et al., *AJR*, 173, 119-125, (Jul. 1999).
Norfray et al., *AJR*, 182(3), 3-13, (Jan. 2004).
Norfray et al., *Journal of Computer Assisted Tomography*, 23(6), 994-1003 (1999).
Norfray, et al., *Pediatric Neurosurgery*, 4th Edition, Ch. 110, McLone (ed), 1189-1203 W.B. Sunders Co. (2001).
Norfray et al., *ARRS Annual Meeting*, (May 4-9, 2003) 1 page Abstract.
Petersen et al., *British Journal of Cancer*, 89, (Suppl. 2) (2003) S25-S35 Abstract.
Petruzelka et al. *I British Journal of Cancer*, 89, (Suppl. 2) (2003) S25-S35 Abstract.
Petruzelka et al. *II British Journal of Cancer*, 89, (Suppl. 2) (2003) S25-S35 Abstract.
Podo, *NMR in Biomedicine*, 12, 413-429 (1999).
Pollard, *Cell Biology*, Elsevier, Inc., Ch. 49, 767-782 (2004).
Ranson et al., *Journal of Clinical Oncology*, 20(9), 2240-2250 (May 1, 2002).
Razis et al., *British Journal of Cancer*, 89, (Suppl. 2) (2003) S25-S35 Abstract.
Reck et al., *British Journal of Cancer*, 89, (Suppl. 2) (2003) S25-S35 Abstract.
Ross et al. *Arch. Surg.*, 122, 1464-1469 (Dec. 1987).
Ross, *The Biochemistry of Living Tissues: Examination by MRS*, 215-219 (1992).
Ross et al., *Magnetic Resonance Quarterly*, 10, 191-247 (1994).
Ross et al., *Journal of Computer Assisted Tomography*, 13(2), 189-193, (Mar./Apr. 1989).
Ross et al., *The Lancet*, 641-646 (Mar. 1984).
Ruiz-Cabello, *NMR in Biomedicine*, 5, 226-233 (1992).
Schwarz et al., *The British Journal of Radiology*, 75, 959-966 (Dec. 2002).
Schmitt et al., *Journal of Pathology*, 187, 127-137 (1999).
Sierko et al., *Semin. Thromb. Hemost.*, 30(1), 95-108 (2004).

Stein et al., *British Journal of Cancer*, 89, (Suppl. 2) (2003) S25-S35 Abstract.
Taga et al. *International Journal of Cancer* 98(5), 690-697 (Apr. 10, 2002) Abstract.
Tang et al., Semin. Thromb. Hemost. 30, 109-117 (2004).
van der Kamp et al., *British Journal of Cancer*, 89, (Suppl. 2) (2003) S25-S35 Abstract.
van Zandwijk, *I British Journal of Cancer*, 89, (Suppl. 2) (2003) S25-S35 Abstract.
van Zandwijk, *II British Journal of Cancer*, 89, (Suppl. 2) (2003) S25-S35 Abstract.
Vincent, *British Journal of Cancer*, 89, (Suppl. 2) (2003) S25-S35 Abstract.
Wojtukiewicz, et al. *Semin. Thromb. Hemost.* 30(1), 5-20 (2004).
Wojtukiewicz et al., *Semin. Thromb. Hemost.* 30(1), 145-156 (2004).
Yamanaka et al. *Drugs today*, 40 (11), 931-914 (Nov. 2004) Abstract.
Yu et al., *Semin. Thromb. Hemost.* 30(1), 21-30 (2004).
Bernales, S. et al., Intracellular signaling by the unfolded protein response, *Annu. Rev. Cell Dev. Biol.*, 2006, 22:487-508.
Clemens, M.J. et al., Translation initiation factor modifications and the regulation of protein synthesis in apoptotic cells, *Cell Death and Differentiation*, 2000, 7: 603-615.
European Patent Office, extended European Search Report relative to cognate European Patent Application No. 05778030.6, mailed Mar. 3, 2010.
European Patent Office, Office Communication relative to cognate European Patent Application No. 05778030.6, mailed Jun. 14, 2010.
European Patent Office, extended European Search Report relative to related European Patent Application No. 06733897.0, mailed Feb. 20, 2009.
European Patent Office, Office Communication relative to related European Patent Application No. 06733897.0, mailed Jun. 18, 2009.
European Patent Office, extended European Search Report relative to related European Patent Application No. 06740479.8, mailed Sep. 17, 2009.
European Patent Office, Office Communication relative to related European Patent Application No. 06740479.8, mailed Dec. 8, 2009.
Indian Patent Office, Examination Report relative to related Indian Patent Application No. 1358/MUMNP/2007, mailed Nov. 23, 2010.
Schneider-Poetsch, T. et al., Inhibition of eukaryotic translation elongation by cycloheximide and lactimidomycin, *Nat Chem Biol*, Mar. 2010, 6(3): 209-217.
Sobell, Henry M., Actinomycin and DNA transcription, *Proc. Natl. Acad. Sci. USA*, Aug. 1985, 82: 5328-5331.
USPTO, Office Action relative to U.S. Appl. No. 10/946,741 (now U.S. Patent No. 7,289,840), mailed Jun. 14, 2006.
USPTO, Office Action relative to U.S. Appl. No. 10/946,741 (now U.S. Patent No. 7,289,840), mailed Jan. 11, 2007.
USPTO, Office Action relative to U.S. Appl. No. 11/053,059 (now U.S. Patent No. 7,622,102), mailed Jun. 15, 2009.
USPTO, Office Action relative to U.S. Appl. No. 11/193,037 (now abandoned), mailed Jan. 26, 2007.
USPTO, Office Action relative to U.S. Appl. No. 11/193,037 (now abandoned), mailed Sep. 11, 2007.
USPTO, Office Action relative to U.S. Appl. No. 11/622,321 (now U.S. patent No. 7,771,706), mailed Sep. 14, 2009.
USPTO, Office Action relative to U.S. Appl. No. 11/622,321 (now U.S. patent No. 7,771,706), mailed Mar. 1, 2010.
USPTO, Office Action relative to co-pending U.S. Appl. No. 11/397,877, mailed Feb. 3, 2009.
USPTO, Office Action relative to co-pending U.S. Appl. No. 11/397,877 mailed Feb. 19, 2010.
Blankenberg et al., Detection of apoptotic cell death by proton nuclear magnetic resonance spectroscopy, *Blood*, 87: 1951-1956 (1996).
Blankenberg et al., Quantitative analysis of apoptotic cell death using proton nuclear magnetic resonance spectroscopy, *Blood*, 89 (10): 3778-3786 (May 15, 1997).
Bursch et al., Programmed cell death (PCD): apoptosis, autophagic PCD, or others?, *Annals N.Y. Academy of Science*, 926: 1-13 (Dec. 2000).
European Patent Office, Office Communication relative to related European Patent Application No. 06740479.8, mailed Apr. 18, 2011.
Ferreira et al., Apoptosis: target of cancer therapy, *Clinical Cancer Research*, 8: 2024-2034 (Jul. 2002).
Gerdes, J. et al., Production of a mouse monoclonal antibody reactive with a human nuclear antigen associated with cell proliferation, *Int. Journal Cancer*, 31: 13-20, 1983.
Lindskog et al., Predicting resistance or response to chemotherapy by proton magnetic resonance spectroscopy in neuroblastoma, *Journal of the National Cancer Institute*, 96 (19): 1457-1466 (2004).
Maiuri et al., Self-eating and self-killing: crosstalk between autophagy and apoptosis, *Nature Reviews/Molecular Cell Biology*, 8: 741-752 (Sep. 2007).
Meisamy et al., Neoadjuvant chemotherapy of locally advanced breast cancer: predicting response with in vivo $^1$H MR spectroscopy—a pilot study at 4 T$^1$, *Radiology*, 233: 424-431 (2004).
Mohamad et al., Mitochondrial apoptotic pathways, *Biocell*, 29(2): 149-161 (2005).
Schmitt et al., Apoptosis and therapy, *Journal of Pathology*, 187: 127-137 (1999).
Scott et al., $^{13}$C-NMR investigation of protein synthesis during apoptosis in human leukemic cell lines, *Journal of Cellular Physiology*, 181: 147-152 (1999).
Shaffer et al., XBP1, downstream of blimp-1, expands the secretory apparatus and other organelles, and increases protein synthesis in plasma cell differentiation, *Immunity*, 21: 81-93 (Jul. 2004).
USPTO, Office Action relative to related U.S. Appl. No. 11/397,877, mailed Apr. 27, 2011.
Chen et al., "The HSP90 family of genes in the human genome: Insights into their divergence and evolution," *Genomics*, vol. 86, pp. 627-637 (2005).
Citri et al., "Hsp90 Recognizes a Common Surface on Client Kinases," *The Journal of Biological Chemistry*, vol. 281, No. 20, pp. 14361-14369 (May 19, 2006).

* cited by examiner

METHOD FOR MONITORING EARLY TREATMENT RESPONSE

CROSS-REFERENCE TO RELATED APPLICATIONS

This patent application claims the benefit of copending U.S. patent application Ser. No. 10/946,741, filed on Sep. 22, 2004, the disclosure of which is incorporated by reference.

FIELD OF THE INVENTION

This invention pertains to a method for monitoring early response to cancer treatment, particularly in a treatment involving cell surface receptor inhibitors. The method involves the use of Magnetic Resonance Spectroscopy (MRS).

BACKGROUND OF THE INVENTION

Some of the common approaches to cancer treatment include surgery, radiation therapy, and chemotherapy. Radiation therapy and chemotherapy are effective if they are capable of killing the tumor cells; i.e., when they act as cytotoxic agents. Typically, the response to radiation therapy or chemotherapy is monitored by magnetic resonance imaging (MRI) of the tumor, wherein a decrease in tumor size is indicative of positive response to treatment.

MRS has been proposed as a tool for obtaining information on cellular metabolism; see, for example, Norfray, J. et al., Ch. 110 in *Pediatric Neurosurgery*, 4$^{th}$ ed., McLone, D. G., et al. (Eds), W.B. Saunders Co. (2001). MRS also has been proposed for diagnosing the treatment response of tumors with cytotoxic agents; see, for example, Fulham, M. J., et al., *Radiology*, 185, 675-686 (1992), which discloses that brain tumor metabolism was studied with $^1$H MRS before and after treatment with radiation therapy. MRS permits non-invasive examination of metabolic characteristics of human cancers in a clinical environment. Accessible nuclei include $^{31}$P, $^{13}$C, $^1$H, and $^{23}$Na. $^{31}$P MRS contains information about energy status (phosphocreatine, inorganic phosphate, and nucleoside triphosphates), phospholipids metabolites (phosphomonoesters and phosphodiesters), intracellular pH (pH NMR), and free cellular magnesium concentration (Mg$^{2+}$ f). Water-suppressed $^1$H MRS shows total choline, total creatine, lipids, glutamate, inositols, lactate, and the like. Negendank, W., *NMR in Biomedicine*, 5, 303-324 (1992).

Further, U.S. Pat. No. 6,681,132 (Katz et al.) discloses a method for determining the effectiveness of chemotherapy comprising administering a dose of a cytotoxic antineoplastic agent to a subject prior to surgical removal of a cancerous tumor, acquiring magnetic resonance data from the subject, and determining whether the treatment has affected the population of a nuclei, particularly $^{23}$Na. Negendank, W., supra, provides a review of various studies of human tumors by MRS.

See also Ross, B. et al., *The Lancet*, 641-646 (1984) discusses monitoring response to cytotoxic chemotherapy of intact human tumors by $^{31}$P MRS; Griffiths, J. R. et al., *The Lancet*, 1435-36, Jun. 25, 1983 discloses the use of $^{31}$P MRS to follow the progress of a human tumor during chemotherapy with doxorubicin; Ross, B. et al., *Arch. Surg.*, 122, 1464-69 (1987) discloses the monitoring of chemotherapeutic treatment response of osteosarcoma and other neoplasms of the bone by $^{31}$P MRS; and Norfray, J. F. et al., *J. Computer Assisted Tomography*, 23(6), 994-1003 (1999) discloses an MRS study of the neurofibromatosis type 1 intracranial lesions.

More recently, peptide inhibitors, e.g., cell surface receptor inhibitors have been proposed for cancer treatment. See, for example, Blackledge, G. et al., *British J. Cancer*, 90, 566-572 (2004), which discloses that the epidermal growth factor receptor (EGFR) is a promising target for cancer therapy and that most advanced in development are the EGFR tyrosine kinase inhibitors (TKI's) gefitinib (Iressa, ZD 1839) and erlotinib (Tarceva, OSI-774), and the monoclonal antibody cetuximab (Erbitux, IMC-C225); Katz, A. et al., *British J. Cancer*, 89 (suppl. 2) S15-S18 (2003), which discloses the quality-of-life benefits and evidence of antitumor activity for patients with brain metastases treated with gefitinib; and Ranson, M. et al., *J. Clin. Oncol.*, 20, 2240-50 (2002) which discloses that gefitinib is well tolerated and active in patients with solid, malignant tumors. However, the peptide receptor inhibitors have a positive response in only 15 to 50% of the patients treated.

The peptide inhibitors are cytostatic rather than cytotoxic; accordingly, classical signs of treatment response, e.g., decreased tumor size or decreased enhancement, common with cytotoxic agents, may not be present with cytostatic peptide inhibitors. Accordingly, classical imaging techniques such as MRI alone may not be suitable or adequate to monitor treatment response.

While MRS is effective as a tool for monitoring treatment response, the disclosures in the art show that it has been applied to monitor the response to cytotoxic agents (radiation and chemotherapy). In many cases, a detectable change in tumor size is observed only after a significantly long period of time, for example, after treatment for a period of about 3 months or more. Such long periods of time could be harmful to the patient, especially if the treatment has not been effective or only partially effective, such as, for example, treatments involving the use of peptide inhibitors; during this long period of time, tumor cells could multiply or metastasize, and lead to worsening of the patient's condition.

The foregoing shows that there exists a need for a method where an early treatment response can be monitored, especially where the treatment involves cell surface receptor inhibitors. Accordingly, the present invention provides such a method. This and other advantages of the invention, as well as additional inventive features, will be apparent from the description of the invention provided herein.

BRIEF SUMMARY OF THE INVENTION

The invention provides a method for monitoring early treatment response of a cancer treatment comprising measuring by MRS, the amount of Choline present in the cancerous tissue before and after treatment; the treatment comprises administration of a cell surface receptor inhibitor, whereby a decrease in the amount of Choline after treatment is indicative of a positive response. In accordance with the invention, diagnosed cancers can be monitored by following cell membrane metabolism utilizing the Choline peak on $^1$H M spectroscopy. The Choline peak represents the visible mobile Choline forming the plasma and organelle cell membranes. A decrease in the Choline identifies treatment response; an increase in the Choline peak identifies treatment failure.

The present invention provides several advantages, for example, the amount of Choline changes prior to classical imaging findings, and the MRS peak corresponding to Choline changes even with a treatment based on cytostatic peptide inhibitors. The present invention offers the combined advantages of MRI and MRS and provides a method to monitor early treatment response. The present invention also provides a method for monitoring cancer treatment. In addition, the present invention provides for a method for monitoring protein translation in an animal having a cancerous tissue comprising administering a cell surface receptor inhibitor to the animal and measuring, by Magnetic Resonance Spectroscopy, the amount of Choline present in the cancerous tissue before and after administering the cell surface receptor inhibitor.

DETAILED DESCRIPTION OF THE INVENTION

The present invention is predicated on monitoring changes in the amount of one or more metabolites occurring in an internal cell membrane, for example, changes induced by the down regulation of one or more of the intracellular organelles and their secretory granules and transport vesicles. The internal cell membranes, which constitute nearly 90% of the total cell membranes, form the membranes of the nucleus, the mitochondria, the lysosomes, the peroxisomes, the endoplasmic reticulums, the Golgi apparatus, the secretory granules, and the transport vesicles. The cell surface receptor inhibitors down-regulate the intracellular organelles and their secretory granules and transport vesicles.

Accordingly, the present invention provides a method for monitoring early treatment response of a cancer treatment comprising measuring, by Magnetic Resonance Spectroscopy (MRS), the amount of Choline present in the cancerous tissue before and after treatment; the treatment comprises administration of a cell surface receptor inhibitor, whereby a decrease in the amount of Choline after treatment is indicative of a positive response. MRS can be based on the resonance of any suitable nuclei; for example, nuclei selected from the group consisting of $^{31}P$, $^{1}H$, $^{13}C$, and $^{23}Na$, and any combination thereof; preferably, $^{1}H$.

A decrease in the amount of Choline occurs very early as a result of the down-regulation. Since Choline contains 9 protons per molecule (as trimethylamines or trimethylammonium salts), the Choline signal is amplified nine-fold. Since up to 90% of the cell membranes can be down regulated in a tumor, MRS provides a sensitive method to monitor early treatment response.

The term "Choline" herein is used to denote choline $((CH_3)_3N^+CH_2CH_2OH)$, a derivative of choline, or a combination of choline and/or one or more derivatives of choline. Examples of choline derivatives include lysophosphatidylcholine, or glycerophosphocholine, phosphomonoesters of choline (e.g., phosphocholine), phosphodiesters of choline (e.g., phosphatidylcholine), sphingomyelin, phosphoethanolamine, glycerophosphoethanolamine, or any combination thereof. In an embodiment of the invention, the term "Choline" represents the sum of choline and all choline derivatives (or total choline), for example, the sum of choline and phosphocholine. Phosphoserine and glycerophosphoserine also can be monitored Ruiz-Cabello, J. et al., *NMR in Biomedicine*, 5, 223-233 (1992); Podo, F., *NMR in Biomedicine*, 12, 413-439 (1999); and Blüms, S. et al., *Magn. Reson. Med.*, 42, 643-654 (1999).

An embodiment of the present invention also provides for a method for monitoring protein translation in an animal having a cancerous tissue comprising administering a cell surface receptor inhibitor to the animal and measuring, by Magnetic. Resonance Spectroscopy, the amount of Choline present in the cancerous tissue before and after administering the cell surface receptor inhibitor. The current invention can be used for monitoring protein translation. Choline visualizes cellular membranes. The quantity of choline directly correlates with the amount of intracellular organelles, which make up 90% of cell membranes. Some organelles, such as rough endoplasmic reticuliums, are the site of protein synthesis. Protein synthesis involves the translation of the RNA nucleotide sequences into protein amino acid sequences. Protein translation is one of the three steps in Francis Crick's central dogma of molecular biology, i.e., DNA is a template for RNA transcription and then RNA is a template that regulates protein translation. Some of the proteins synthesized in the cell's organelles are inserted into cellular membranes, while other proteins synthesized in the cell's organelles are secreted as part of a coordinated cellular process. An increase in protein synthesis increases mass of these organelles and a decrease in protein synthesis decreases the mass of these organelles. Thus, the cellular Choline level also reflects cellular protein synthesis. Accordingly, drugs up-regulating or down-regulating protein translation can be monitored by following Choline levels (resulting from an increase or decrease in organelles). Therefore, the current invention can monitor early treatment response by quantifying Choline of intracellular organelles linked to protein synthesis (translation). Further, the effect of drugs that can interrupt or up-regulate DNA replication (which requires protein translation) or RNA transcription (which results in protein translation), can be monitored by the current invention with protein translation visualized by decreases or increases in Choline.

The amount of Choline can be measured by MRS in any suitable manner. For example, the amount of Choline can be measured by measuring the height of a peak or peaks corresponding to Choline. In another embodiment, the amount of Choline can be measured by measuring the area under a peak or peaks corresponding to Choline. In yet another embodiment, the amount of Choline can be measured by measuring the ratio of the height of a peak or peaks corresponding to Choline relative to the height of a peak or peaks of an internal standard. In a further embodiment, the amount of Choline can be measured by measuring the ratio of the area under a peak or peaks corresponding to Choline relative to the area under a peak or peaks of an internal standard.

Any suitable internal standard can be used. For example, the internal standard is total creatine when the MRS is based on $^{1}H$ resonance, or internal standard is adenosine triphosphate (ATP) when the MRS is based on $^{31}P$ resonance. The term "total creatine" refers to the combination of creatine and phosphocreatine. Creatine is buffered in cell systems; accordingly, the amount of creatine remains substantially constant.

It is contemplated that the present inventive method is applicable to monitoring early treatment response wherein the treatment involves inhibition of any suitable cell surface receptor, for example, the cell surface receptor is vascular endothelial growth factor receptor (VEGFR) or epidermal growth factor receptor (EGFR), fibroblast growth factor receptor (FGFR), platelet derived growth factor receptor (PDGFR), stem cell receptor (SCFR), nerve growth factor receptor (NGFR), hepatocyte growth factor (HGFR), insulin growth factor receptor (IGFR), a receptor having a tyrosine kinase domain, a receptor having a serine threonine kinase domain, a receptor utilizing a cytoplasmic tyrosine kinase, an angiogenesis factor receptor, or integrin receptor, preferably the EGFR.

In accordance with an embodiment of the present invention, inhibition of the cell surface receptor causes an interruption in an up-regulated intracellular organelle; for example, an interruption in the function of the secretory granules and/or the transporting vesicles. In accordance with another embodiment of the invention, inhibition of the cell surface receptor causes an interruption in the function of the Golgi apparatus. In further embodiments of the invention, inhibition of the cell surface receptor causes an interruption in the function of the lysosomes, the endoplasmic reticulum, the mitochondrion, the nucleus, and/or the peroxisomes.

Examples of suitable cell surface receptor inhibitors include gefitinib, erlotinib, cetuximab, canertinib, EKB-569, lapatinib, and any combination thereof. It has been reported that gefitinib (ZD1839) is an EGFR-tyrosine kinase inhibitor (EGFR-TKI) that causes inhibition of EGF-stimulated autophosphorylation in cell lines at submicromolar concentrations. Ranson et al., supra. It has been reported that ZD1839 has demonstrated, in preclinical studies, antitumor activity against a variety of human cancer cell lines expressing EGFR, including ovarian, breast, and colon, and that it is active in a range of xenograft models, including colon cancer, non-small cell lung cancer (NSCLC), and prostate cancer. Ranson et al., supra. See also, Lynch et al., *The New England J. Medicine*, 350, 2129-2139 (May 20, 2004), which discloses that about 10% of the NSCLC patients treated with gefitinib have a rapid and often dramatic clinical response. Erlotinib is also an EGFR-TKI; it is being studied in many different cancers including breast cancer. Cetuximab is a monoclonal antibody that targets EGFR and is approved for colorectal metastatic cancer. Canertinib is also an EGFR-TKI and is targeted for cancer treatment. EKB-569 is an investigational cytostatic agent and an EGFR kinase inhibitor used to treat a variety of tumor cells that overexpress EGFR and Her2, including non-small cell lung and colorectal cancers. Lapatinib is an EGFR and ErbB-2 (Her2/neu) dual tyrosine kinase and is considered for treatment of solid tumors such as breast and lung cancer.

Protein tyrosine kinases are enzymes that provide a central switch mechanism in cellular signal transduction pathways. As such they are involved in many cellular processes such as cell proliferation, metabolism, survival, and apoptosis. Several protein tyrosine kinases are known to be activated in cancer cells and to drive tumor growth and progression. Therapeutic strategies include blocking kinase-substrate interaction, inhibiting the enzyme's adenosine triphosphate (ATP) binding site and blocking extracellular tyrosine kinase receptors on tumor cells.

The erbB or HER family of transmembrane tyrosine kinase receptors, especially receptors erbB1 (or EGFR) and erbB2 (or Her2/neu), has been identified as an important therapeutic target in a number of cancers. Her2/neu, for example, is overexpressed in around 20% to 30% of patients with aggressive breast cancer, while EGFR is overexpressed in several solid tumours.

In accordance with the present invention, any suitable cancer or tumor can be treated, for example, a cancer selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, pancreatic cancer, neuroblastoma, mesothelioma, prostate cancer, bone cancer, kidney cancer, and heptocellular cancer.

In accordance with the present inventive method, early treatment response can be measured within a period of about 168 hours, preferably about 24 hours, and more preferably about 12 hours, of the treatment. For example, the response can be monitored every 12, 24, 36, 48, 60, 72, 84, 96, 108, 120, 132, 144, 156, or 168 hours, or any combination thereof, after administration of the peptide inhibitor.

Treatment response can also be documented using the current invention within 24 to 168 hours by monitoring protein translation. This embodiment utilizes a magnetic resonance magnet, equal to or greater than 1.5 Tesla, uses existing software and coils which are commercially available, has high spatial resolution, lacks radiation, employs user-friendly automatic sequences, allows non-invasive sequential analysis of drug doses/combinations, provides quantification from multi-sites, and can be employed with a plurality of drugs for trials. This embodiment can monitor treatment responses in vivo and in vitro, in humans and laboratory animals, as well as, in tissues and perfused cell extracts. This embodiment quantifies normal protein translation, as well as the amplified protein translation seen in cancer and inflammation. Since protein translation occurs in all cells, all cancer histologies can be studied. This embodiment is applicable to cytostatic (e.g., growth factor inhibitors) and cytotoxic drugs (e.g., anti-apoptosis receptor inhibitors). In addition, drugs augmenting protein translation can be monitored. Potential uses of this embodiment include, but are not limited to, drug development and documenting interruption of signaling pathways.

The present invention also provides a method for monitoring cancer treatment comprising: (a) localizing a tumor in a patient; (b) selecting a region of interest (ROI) of the tumor; (c) obtaining magnetic resonance spectra (MRS) of the ROI; (d) measuring the amount of Choline from the MRS spectra; (e) initiating treatment comprising administering a cell surface receptor inhibitor; (f) obtaining MR spectra of the tumor at the same ROI within a period of 7 days, preferably 3 days, and more preferably within 1 day, of initiating treatment; (g) measuring the amount of Choline from the MR spectra; and (h) comparing the amount of Choline obtained before treatment with the amount of Choline obtained after treatment; whereby a decrease in the amount of Choline after treatment is indicative of a positive response to treatment.

The basis for clinical MR studies (e.g., MRS or MRI) is the one of the nuclei, for example, the hydrogen nucleus—the proton. The same machinery is used for these studies. They differ in the software manipulation of the emitted radiofrequency (RF) from the H nuclei. In MRI, the signal is used to create the image; in MRS, the signal is used to create the spectrum. Fourier Transform principle is the basis of the computer that allows the MRS software to separate the individual RFs within the signal. The spectrum therefore represents the different RFs being emitted within the selected region of interest (ROI). The points along the horizontal axis of the spectrum represent specific RFs emitted from each metabolite. The vertical axis of the spectrum is proportional to the amount of each metabolite forming the area beneath the RF peaks. Spectra can be obtained on 0.5 to 2.0 T M scanners, although high-field strength scanners provide better definition of the spectra. Spectra obtained with different-strength scanners can be compared on a scale in parts per million (ppm) along the horizontal axis because metabolites always reside at one or more specific sites, for example, alanine resides at 1.47, N-acetylaspartate resides at 2.0 and 2.6 ppm, creatine resides at 3.0 and 3.9 ppm, Choline resides at 3.2 ppm, and water resides at 5.0 ppm.

Any suitable MR spectrometer can be used in the practice of the present invention. Clinical MR spectra can be obtained on MR scanners, for example, utilizing the clinical spectroscopy package called proton brain exam/single voxel (PROBE/SV) developed by General Electric Medical Systems (Milwaukee, Wis.) for use with GE's 1.5 Tesla (T) MR scanner. See Norfray, J. et al., supra, and Norfray, J. F. et al., supra, for procedures for obtaining MR spectra, identification of the peaks corresponding to metabolites such as Choline, creatine, and others, and ratio of the peaks. See also Danielsen and Ross, Magnetic Resonance Spectroscopy Diagnosis of Neurological Diseases, Marcel Dekker, Inc. (1999); Ross, B.

et al., *Magnetic Resonance Quarterly*, 10, 191-247 (1994); and Ross et al., U.S. Pat. No. 5,617,861. Based on the information in the above publications, as well as information available in the art, those of skill in the art should be able to practice the invention on all types of tumors in accordance with the present invention.

The present invention can be carried out in any suitable manner, for example, as follows. Prior to initiating a therapy on a patient, the tumor is localized. Thus, for example, magnetic resonance images (MRI's) of the tumor, e.g., brain metastasis, breast malignancy, or bone tumor, with axial, sagittal, and coronal T1 and T2 images are obtained with and without contrast. A region of interest (ROI) of tumor is selected. This can be carried out based on the MRI findings to determine the tumor volume and location to be studied. MR spectra of the ROI are obtained within the tumor utilizing short and/or long TE (echo time) pulse sequences. The spectra obtained are interpreted. The peak corresponding to Choline is identified, e.g., at a chemical shift of 3.22 ppm. Based on the Choline peak, the amount of total cellular membranes is determined from either the height of the peak or the area under the peak. An internal or external standard is identified in the ROI. An example of an internal standard is creatine or total creatine. An example of an external standard is 100% 2-(trimethylsilyl)ethanol (TSE), which may be taped to the head coil of the MR spectrometer. Kreis, R. et al., *J. Magnetic Resonance*, Series B 102, 9-19 (1993). The ratio of the Choline to the standard is calculated. The Choline to creatine ratio represents a measure of the total cell membranes within the ROI of the tumor prior to treatment.

The treatment of the tumor is initiated by administering an effective amount of the receptor inhibitor starting from time zero. The early treatment response can be monitored, for example, at 24 hours (day 1) to 168 hours (day 7), as follows. The tumor is localized utilizing the same MRI pulse sequences as prior to the treatment. The same ROI is selected within the tumor. MR spectra of the tumor are obtained utilizing the same pulse sequences, the same TR (relaxation time), TE (echo time), phases, and frequency averages. The MR spectra are interpreted as before and the Choline to creatine ratios (e.g., height or area ratios) are calculated.

If the observed decrease in the Choline to creatine ratio is 15% or more, preferably 20% or more, and more preferably 25% or more relative to pre-treatment condition, then it can be concluded that an early response is positive and tumor regression has been achieved. The early decrease in the Choline to creatine ratio identifies a decrease in the intracellular cell membranes, for example, a decrease in the organelles and their granules and/or vesicles. If the ratio of Choline to creatine increases, e.g., a 15% or more, preferably 20% or more, and more preferably 25% or more, of an early increase in the ratio is observed, the increase identifies an increase in the intracellular membranes, for example, an increase in the organelles and their granules and/or vesicles.

The present invention further provides a method for determining effectiveness of a molecule as a drug for treating cancer comprising administering an amount of the molecule to an animal having a cancerous tissue and measuring, by Magnetic Resonance Spectroscopy, the amount of Choline present in the cancerous tissue before and after administering the molecule, wherein the molecule comprises a cell surface receptor inhibitor, whereby a decrease in the amount of Choline after administering the molecule is indicative of its effectiveness. The animals to be used in the present method can be, for example, mammals such as mice, rats, horses, guinea pigs, rabbits, dogs, cats, cows, pig, and monkeys. The amount of cell surface receptor inhibitor will vary with a number of factors, e.g., weight of the animal, type of cancer, and severity of cancer, and is within the skill of the artisan. The potential drug can be administered by any suitable route of administration, e.g., oral, aerosol, parenteral, subcutaneous, intravenous, intraarterial, intramuscular, interperitoneal, rectal, and vaginal routes. The cancer can be natural or induced. Thus, effectiveness of a potential drug can be determined within a relatively short period of time, for example, within 12-168 hours, preferably 12-24 hours.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having,""including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for monitoring protein translation in an animal having a cancerous tissue comprising:
    administering a cell surface receptor inhibitor of a cell surface receptor selected from the group consisting of vascular endothelial growth factor receptor (VEGFR), epidermal growth factor receptor (EGFR), fibroblast growth factor receptor (FGFR), platelet derived growth factor receptor (PDGFR), stem cell receptor (SCFR), nerve growth factor receptor (NGFR), hepatocyte growth factor (HGFR), insulin growth factor receptor (IGFR), a receptor having a tyrosine kinase domain, a receptor having a serine threonine kinase domain, a receptor utilizing a cytoplasmic tyrosine kinase, an angiogenesis factor receptor, and integrin receptor to the animal;

measuring, by Magnetic Resonance Spectroscopy, the amount of Choline present in the intracellular membranes of the organelles of the cancerous tissue before and after administering the cell surface receptor inhibitor, obtaining a difference between the amounts of Choline, and correlating the difference to protein translation.

2. The method of claim 1, wherein the MRS is based on the resonance of nuclei selected from the group consisting of $^{31}$P, $^{1}$H, and $^{13}$C and any combination thereof.

3. The method of claim 2, wherein the MRS is based on $^{1}$H resonance.

4. The method of claim 1, wherein measuring the amount of Choline comprises measuring the height of a peak corresponding to Choline.

5. The method of claim 1, wherein measuring the amount of Choline comprises measuring the area under a peak corresponding to Choline.

6. The method of claim 1, wherein measuring the amount of Choline comprises measuring the ratio of the height of a peak corresponding to Choline relative to the height of peak of an internal standard.

7. The method of claim 6, wherein the internal standard is total creatine when the MRS is based on $^{1}$H resonance.

8. The method of claim 6, wherein the internal standard is adenosine triphosphate (ATP) when the MRS is based on $^{31}$P resonance.

9. The method of claim 1, wherein measuring the amount of Choline comprises measuring the ratio of the area under a peak corresponding to Choline relative to the area under a peak of an internal standard.

10. The method of claim 9, wherein the MRS is based on $^{1}$H resonance and the internal standard is total creatine.

11. The method of claim 1, wherein measuring the amount of Choline comprises measuring the amount of choline, phosphocholine, phosphatidylcholine, lysophosphatidylcholine, glycerophosphocholine, phosphomonoesters of choline, phosphodiesters of choline, phosphoethanolamine, glycerophosphoethanolaminc, or any combination thereof.

12. The method of claim 1, wherein the amount of Choline is measured within a period of about 168 hours of said administering of a cell surface receptor inhibitor.

13. The method of claim 12, wherein the amount of Choline is measured within a period of about 24 hours.

14. The method of claim 13, wherein the amount of Choline is measured within 12 hours of said administering of a cell surface receptor inhibitor.

15. The method of claim 1, wherein the cell surface receptor inhibitor is selected from the group consisting of gefitinib, erlotinib, cetuximab, canertinib, EKB-569, lapatinib, and any combination thereof.

16. The method of claim 1, wherein the cancer is selected from the group consisting of brain cancer, colorectal cancer, breast cancer, acute leukemia, lung cancer, kidney cancer, squamous cell cancer, testicular cancer, stomach cancer, melanoma, sarcomas, ovarian cancer, non-small cell lung cancer, esophageal cancer, pancreatic cancer, neuroblastoma, mesothelioma, prostate cancer, bone cancer, and hepatocellular cancer.

17. The method of claim 1, wherein inhibition of the cell surface receptor causes an interruption in an up-regulated intracellular organelle.

18. The method of claim 17, wherein the interruption in the up-regulated intracellular organelle takes place in the secretory granules.

19. The method of claim 17, wherein the interruption in the up-regulated intracellular organelle takes place in the transporting vesicles.

20. The method of claim 1, wherein inhibition of the cell surface receptor causes an interruption in a function of the Golgi apparatus.

21. The method of claim 1, wherein inhibition of the cell surface receptor causes an interruption in a function of the lysosomes.

22. The method of claim 1, wherein inhibition of the cell surface receptor causes an interruption in a function of the endoplasmic reticulum.

23. The method of claim 1, wherein inhibition of the cell surface receptor causes an interruption in a function of the mitochondrion.

24. The method of claim 1, wherein inhibition of the cell surface receptor causes an interruption in a function of the nucleus.

25. The method of claim 1, wherein inhibition of the cell surface receptor causes an interruption in a function of the peroxisomes.

* * * * *